United States Patent [19]

Maffia et al.

[11] Patent Number: 5,162,593
[45] Date of Patent: Nov. 10, 1992

[54] TERTIARY BUTYL ALCOHOL PREPARATION

[75] Inventors: Gennaro J. Maffia, Newtown Square; John C. Jubin, West Chester, both of Pa.

[73] Assignee: Arco Chemical Technology, L.P., Wilmington, Del.

[21] Appl. No.: 797,649

[22] Filed: Nov. 25, 1991

[51] Int. Cl.⁵ .................. C07C 29/00; C07C 31/12
[52] U.S. Cl. .................. 568/909.8; 568/910
[58] Field of Search ........................ 568/909.8

[56] References Cited

U.S. PATENT DOCUMENTS

| | | | |
|---|---|---|---|
| 3,360,584 | 12/1967 | Kollam | 568/909.8 |
| 3,470,239 | 9/1969 | Russell | 568/909.8 |
| 4,910,349 | 3/1990 | Sanderson et al. | 568/909.8 |
| 4,977,285 | 12/1990 | Marquis et al. | 568/909.8 |
| 4,992,602 | 2/1991 | Sanderson et al. | 568/909.8 |

OTHER PUBLICATIONS

Winkler et al, "Ind. & Eng. Chem.," vol. 53, No. 8, Aug. 1961, pp. 655-658.

*Primary Examiner*—J. E. Evans
*Attorney, Agent, or Firm*—William C. Long

[57] ABSTRACT

TBA is prepared by a process wherein isobutane is continuously oxidized to a TBA/TBHP mixture, TBA is recovered from the mixture and TBHP is recycled to the isobutane oxidation step wherein it is converted to TBA at the isobutane oxidation conditions.

1 Claim, 1 Drawing Sheet

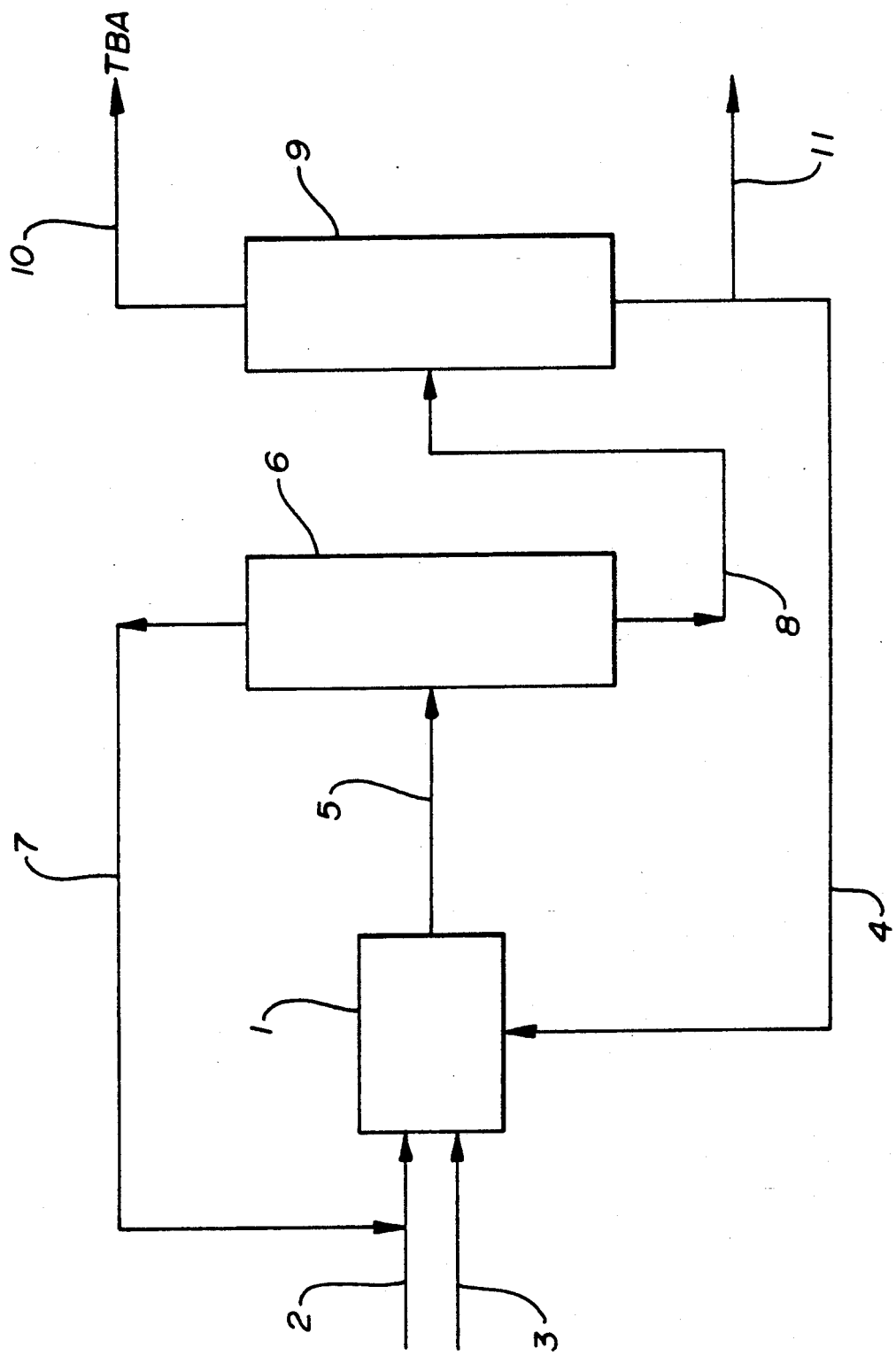

5,162,593

TERTIARY BUTYL ALCOHOL PREPARATION

BACKGROUND OF THE INVENTION

1. Field of the Invention

The present invention relates to the preparation of tertiary butyl alcohol (TBA) by a process wherein isobutane is oxidized to a mixture of tertiary butyl hydroperoxide (TBHP) and TBA, unreacted isobutane is separated from a TBA/TBHP product fraction, TBA is separated from the resulting TBA/TBHP fraction by distillation, and a stream concentrated in TBHP is returned to the isobutane oxidation zone wherein at the isobutane oxidation conditions the TBHP is converted to TBA with a high degree of selectivity.

2. Description of the Prior Art

It is known to oxidize isobutane in the liquid phase to produce a reaction product mixture mainly comprised of TBHP and TBA. See Winkler, et al. U.S. Pat. No. 2,845,461.

A number of patents deal with the catalytic decomposition of hydroperoxides such as TBHP recovered from isobutane oxidation. A series of patents to Sanderson, et al. describes the use of various catalysts to accomplish the TBHP decomposition to TBA. U.S. Pat. No. 4,992,602 uses a metal phthalocyanine catalyst. U.S. Pat. No. 4,910,349 uses a metal phthalocyanine plus rhenium catalyst, U.S. Pat. No. 4,912,266 uses a metal phthalocyanine plus imidazole catalyst, U.S. Pat. No. 4,912,267 uses a base promoted metal phthalocyanine catalyst, U.S. Pat. No. 4,922,033 uses a bidenate promoted ruthenium catalyst, U.S. Pat. No. 4,922,034 uses a metal porphine catalyst, U.S. Pat. No. 4,922,035 uses a promoted metal phthalocyanine catalyst and U.S. Pat. No. 4,922,036 uses a borate promoted metal phthalocyanine catalyst.

Taylor, et al. U.S. Pat. No. 4,551,553 shows the catalytic decomposition of an organic hydroperoxide such as tertiary butyl hydroperoxide using a binary catalyst composed of a mixture of a ruthenium compound with a chromium compound.

Quin U.S. Pat. No. 2,854,487 discloses a process wherein isopropyl benzene hydroperoxides are catalytically decomposed in the presence of hydrogen and a palladium-supported on activated alumina catalyst.

Grane U.S. Pat. No. 3,474,151 discloses that residual quantities of hydroperoxide contaminants present in tertiary butyl alcohol could be thermally decomposed by heating the contaminated tertiary butyl alcohol at a temperature of 375° to 475° F. for about 1 to 10 minutes.

Grane, et al. U.S. Pat. No. 4,294,999 discloses a process wherein isobutane is oxidized in the presence of a solubilized molybdenum catalyst to provide a mixture of TBA, TBHP, methanol, acetone and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,141 by heating the tertiary butyl alcohol at 375° to 475° F. for about 1 to 10 minutes.

Grane, et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decomposed at 250°–350° F. at a pressure lower than the pressure in the oxidation zone. Worell, et al in U.S. Pat. No. 4,296,263 discloses a related process wherein the feedstock is a mixture of normal butane with isobutane and wherein the oxidation catalyst is a soluble form of chromium, cobalt, nickel, manganese, molybdenum or a mixture thereof.

An article entitled "Metal-Catalyzed Epoxidation of Olefins with Organic Hydroperoxides" by Sheldon, et al., *Journal of Catalysts*, 31, 427–437 (1979) on pages 30 and 31, reports on the results obtained by the Metal-Catalyzed Decomposition of Tertiary Butyl Hydroperoxide in the absence of an olefin including the decomposition of tertiary butyl hydroperoxide in solution in benzene in the presence of Mo, Ti, W and Cr catalysts to provide tertiary butyl alcohol and oxygen.

The procedures for producing TBA described by prior workers were generally expensive and complicated, and in many cases involved the use of costly and contaminating catalytic materials.

BRIEF DESCRIPTION OF THE INVENTION

The process of the present invention provides an improved process for the production of TBA whereby isobutane is oxidized in the liquid phase with molecular oxygen to form a reaction product mixture containing TBHP and TBA, unreacted isobutane is separated from the TBHP/TBA reaction products by distillation, the TBHP/TBA mixture is distilled to recover TBA product from a fraction concentrated in TBHP, and the fraction concentrated in TBHP after purging or otherwise removing the heavies is returned to the isobutane oxidation reaction zone wherein at the isobutane oxidation reaction conditions the returned TBHP is selectively and efficiently converted to TBA.

DESCRIPTION OF THE DRAWING

The accompanying drawing illustrates in schematic form practice of the invention.

DETAILED DESCRIPTION

With reference to the attached drawing which illustrates practice of the invention, fresh and recycle isobutane are fed to reaction zone 1 by means of line 2. Also fed to zone 1 is a molecular oxygen stream via line 3 and a concentrated TBHP stream via line 4.

The isobutane oxidation reaction conditions in oxidation zone 1 are those which are normally used for this reaction as described, for example, in Winkler, et al. U.S. Pat. No. 2,845,461. Generally, reaction temperatures in the range of 100° C. to 200° C., preferably 120° C. to 150° C. are employed. Pressures in the range of 300 to 500 psig, preferably 400 to 450 psig are employed. Residence times in the oxidation zone of 3 to 15 hours, preferably 5 to 10 hours are suitable.

It is preferred to use oxygen as the oxidant, although the use of oxygen in admixture with an inert gas such as nitrogen can be used.

Although zone 1 is depicted in the drawing as a single reaction zone, it will be understood that a plurality of zones in series or in parallel may be employed.

A liquid oxidation reaction product stream comprised of unreacted isobutane, TBHP, TBA and oxygen-containing by-products is removed from zone 1 via line 5 and passes to distillation zone 6 wherein the unreacted isobutane is distilled overhead and recycled via line 7 to oxidation zone 1.

Although zone 6 is shown as a single zone, it will be understood that for economic reasons zone 6 can comprise a plurality of separation zones.

Conditions in zone 6 are those conventionally employed including an overhead temperature of 40° C. to 100° C., preferably 50° C. to 70° C., and overhead pressure of 100 to 200 psig, preferably 170 to 185 psig. The liquid bottoms at a temperature of 80° C. to 120° C., preferably 100° C. to 110° C., and pressure 100 to 200 psig, preferably 170 to 185 psig, exits zone 6 via line 8 and passes to distillation zone 9. This liquid stream illustratively comprises by weight about 35 to 55% TBA, 35 to 55% TBHP and 1 to 3% oxygen-containing by-products; residual isobutane is usually less than 1%.

In distillation zone 9 the reaction product mixture is distilled in order to recover a concentrated TBA product overhead and to recover a bottoms stream which is concentrated in TBHP. The TBA distillate stream is separated via line 10 and may be processed in a conventional fashion or it may be converted directly to a more valuable product such as methyl tertiary butyl ether. The TBHP concentrate liquid bottoms stream is separated via line 4 and, as an essential feature of the present invention, at least a portion is recycled to oxidation zone 1.

To control the build-up of heavies, a purge stream is removed via line 11 and processed further if economical, or sent to fuel. The circulating heavies concentration may be reduced if further distillation is performed prior to recycle. This is an optimization and needs to be looked at in cost effectiveness terms.

As an additional feature of the invention, where some TBHP is needed, for example, for the production of propylene oxide in accordance with known technology, sufficient of the concentrated TBHP stream can be removed via line 11 and sent to epoxidation (not shown). By this means, the ratio of TBA to propylene oxide produced can be adjusted within a wide range to meet economic demands.

The TBHP concentrate stream generally comprises by weight about 20 to 70% TBHP, 10 to 50% TBA, and 5 to 35% oxygen-containing impurities.

It is important that great care be exercised as to the distillation in zone 9 since TBHP is highly flammable in concentrated form. An especially preferred method for carrying out the distillation in zone 9 is that which is described in co-pending application Ser. No. 07/645,434 filed Jan. 24, 1991, the disclosure of which is incorporated herein.

Essential to practice of the present invention is the conversion of the TBHP in the concentrate exiting zone 9 via line 4. In accordance with the present invention, it has been found that by recycling this concentrate to oxidation reaction zone 1 that selective conversion of the TBHP to TBA effectively takes place in zone 1 at the conditions which are normally employed for the oxidation of isobutane to a mixture of TBA and TBHP. An added advantage of the process of the invention is that the oxidation rates and selectivities are actually improved by reason of the recycle of the TBHP concentrate to oxidation zone 1.

Although not shown on the attached drawing, it is frequently advantageous to treat the TBHP concentrate in order to remove acidic impurities prior to the recycle to zone 1 since a build-up of such impurities tends to adversely affect the oxidation results achieved in zone 1.

Practice of the present invention has several distinct and important advantages. In the first instance, the isobutane oxidation in zone 1 is significantly improved as a result of practice of the invention. In addition, the necessity for a separate TBHP decomposition step involving a separate reaction zone and the use of expensive contaminating catalysts is avoided. Practice of the present invention is efficient and is believed to provide a distinct economic advantage over the procedures followed by prior workers.

The following example is provided in order to illustrate practice of the invention.

EXAMPLE 1

Referring to the accompanying drawing, isobutane is fed to zone 1 at the rate of 400 mols/hr. via line 2. This isobutane stream represents 100 mols/hr. of net fresh feed and about 300 mols/hr recycle via line 7. Also fed to zone 1 is an oxygen stream at the rate of 60 mols oxygen per hour via line 3. The conditions of the isobutane oxidation maintained in zone 1 are at a temperature of 145° C. and a pressure of 20 atmospheres. Residence time in reaction zone 1 is 8 hours.

Also fed to zone 1 via line 4 is a TBHP concentrate stream containing 35% TBA, 45% TBHP and 20% oxygen-containing impurities, all on a molar basis expressed as $C_4$ equivalents.

A liquid reaction product stream exits zone 1 via line 5 at the rate of 1100 mols/hr. as $C_4$ equivalents and is passed to distillation zone 6. This reaction product stream has a composition of 27% isobutane, 29% TBA, 30% TBHP and 14% oxygen-containing impurities, all on a $C_4$ molar equivalent basis.

Distillation zone 6 has 25 theoretical stages and operates with an overhead temperature of 70° C. and pressure of 180 psig and a bottoms temperature of 104° C. and 183 psig. An overhead isobutane distillate stream comprised of greater than 99% isobutane passes at the rate of 300 mols/hr. via line 7 and is recycled to oxidation zone 1.

The oxidation reaction product stream comprising 40% TBA, 41% TBHP and 19% oxygen-containing impurities passes as the rate of 800 mols/hr. expressed as $C_4$ molar equivalents via line 8 to distillation zone 9.

Distillation zone 9 is a vacuum distillation zone having 30 theoretical stages. The overhead temperature is maintained at 45° C. and 200 mmHg pressure. A TBA product distillate stream is removed via line 10 for recovery. This stream comprises 87% TBA, <1% TBHP and 12% others and is removed at the rate of 80 mols/hr, all on a $C_4$ molar equivalent basis.

A liquid bottoms stream concentrated in TBHP, composition as indicated above, is removed from zone 9 via line 4 and recycled to oxidation zone 1. The TBHP concentrate stream passes to zone 1 via line 4 at the rate of 700 mols/hr. and in zone 1 is decomposed to yield product TBA with a high degree of efficiency and selectivity.

A portion of the bottoms from zone 9 is removed as purge at the rate of 20 mols/hr. via line 11.

Thus, the invention provides an effective means for converting TBHP to TBA without the necessity of major equipment addition or the use of costly additional chemicals.

I claim:

1. In a continuous method for preparing t-butyl alcohol (TBA) wherein isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide (TBHP) and TBA, and wherein unreacted isobutane is continuously separated from said initial reaction mixture in a distillation zone to provide a charge stock comprising a solution of said TBHP in said TBA, the improvement which comprises:

(a) continuously distilling said charge stock in a distillation zone to provide a second distillate TBA fraction and a third distillation fraction concentrated in TBHP,
(b) continuously passing at least a portion of said third distillation fraction to said oxidation reaction zone, and
(c) continuously decomposing TBHP contained in said third distillation fraction to TBA at the liquid phase oxidation reaction conditions in said oxidation reaction zone.

* * * * *